(12) United States Patent
Dumont (10) Patent No.: US 10,765,452 B2
(45) Date of Patent: Sep. 8, 2020

(54) IMPLANTATION DEVICE COMPRISING A SET OF IMPLANTS

(71) Applicant: SEDATELEC, Irigny (FR)

(72) Inventor: François Dumont, Maringes (FR)

(73) Assignee: SEDATELEC, Irigny (FR)

( * ) Notice: Subject to any disclaimer, the term of this patent is extended or adjusted under 35 U.S.C. 154(b) by 125 days.

(21) Appl. No.: 15/741,470

(22) PCT Filed: Jun. 28, 2016

(86) PCT No.: PCT/FR2016/051608
§ 371 (c)(1),
(2) Date: Jan. 2, 2018

(87) PCT Pub. No.: WO2017/001773
PCT Pub. Date: Jan. 5, 2017

(65) Prior Publication Data
US 2018/0360492 A1    Dec. 20, 2018

(30) Foreign Application Priority Data
Jul. 2, 2015   (FR) ..................... 15/56235

(51) Int. Cl.
*A61B 17/34*     (2006.01)
*A61H 39/08*     (2006.01)

(52) U.S. Cl.
CPC ......... *A61B 17/3468* (2013.01); *A61H 39/08* (2013.01); *A61H 39/083* (2013.01); *A61H 39/086* (2013.01); *A61B 2017/3405* (2013.01)

(58) Field of Classification Search
CPC .... A61H 39/08; A61H 39/083; A61H 39/086; A61B 17/3468
See application file for complete search history.

(56) References Cited

U.S. PATENT DOCUMENTS

2005/0067309 A1    3/2005 Choi
2011/0160759 A1*   6/2011 Schraga ............... A61B 5/1411
                                                    606/172

FOREIGN PATENT DOCUMENTS

CN    2083927 U    9/1991
CN    201880014 U   6/2011
(Continued)

OTHER PUBLICATIONS

International Search Report dated Oct. 4, 2016 re: Application No. PCT/FR2016/051608; pp. 1-3; citing: ES 272 596 U, WO 01/39829 A, CN 203 790 289 U, CN 201 880 014 U, US 2005/067309 A1, CN 2 083 927 U, CN 204 293 501 U, KR 2014 0143601 A and KR 2014 0010513 A.

*Primary Examiner* — Thomas McEvoy
(74) *Attorney, Agent, or Firm* — Cantor Colburn LLP (57) ABSTRACT

This implantation device includes: a set of separable implants, a guide member defining a passage for guiding the set of implants in translation towards the outlet orifice, a transmission member for transmitting a pushing force in order to move the set of implants towards an outlet, the transmission member having several successive projections, and a pushing member to allow the practitioner to generate the pushing force. The pushing member includes a bearing part configured to bear against several of the projections during successive movements of the pushing member, the bearing part having in succession a bearing position and a clearing position, and a unidirectional stop element connected to the guide member and configured to have in succession i) a configuration of clearance by a projection and ii) a stop configuration so as to immobilize the transmission member in the inverse direction of the translation towards the outlet.

31 Claims, 7 Drawing Sheets

(56) References Cited

FOREIGN PATENT DOCUMENTS

| | | |
|---|---|---|
| CN | 203790289 U | 8/2014 |
| CN | 204293501 U | 4/2015 |
| ES | 272596 U | 11/1983 |
| FR | 2335201 A1 | 7/1977 |
| KR | 20140010513 A | 1/2014 |
| KR | 20140143601 A | 12/2014 |
| WO | 0139829 A1 | 6/2001 |

\* cited by examiner

IMPLANTATION DEVICE COMPRISING A SET OF IMPLANTS

TECHNICAL FIELD

The present disclosure concerns an implantation device for implanting implants in the body of a living being, either human or animal. The present disclosure concerns in particular an implantation device for implanting acupuncture needles, for example semi-permanent type or permanent type acupuncture needles.

BACKGROUND

The present disclosure applies to the field of the implantation of implants, for example medical implants, in particular to the field of the implantation of acupuncture needles, and more particularly to the field of the implantation of semi-permanent acupuncture needles. For example, the present disclosure applies to the implantation of needles configured for implantation in the auricle.

An acupuncture needle remains implanted only during the acupuncture session, then the acupuncture needle is removed at the end of the acupuncture session. On the contrary, a semi-permanent needle can remain implanted after the acupuncture session, and then be removed later on.

Semi-permanent needles or permanent needles can be implanted in the bodies of living beings, either humans or animals.

FR2335201A1 illustrates an implantation device for implanting a semi-permanent acupuncture needle. The implantation device comprises a pusher to allow the practitioner to generate a pushing force, a transmission member to transmit the pushing force to the semi-permanent acupuncture needle, as well as a guide to guide the acupuncture needle up to an outlet port placed against the epidermis of a patient.

The implantation device and the acupuncture needle are provided in a sterile state and configured for a single use. After having implanted the acupuncture needle, the practitioner recycles or discards the implantation device.

However, in order to implant several acupuncture needles, the practitioner must unpack several needles and then implant them, which induces a waste of time. In addition, these multiple unpackings of needles induce a breaking of the rhythm of the practitioner's gesture, which risks generating an inaccuracy during successive implantations.

SUMMARY

The present disclosure aims in particular to solve, in whole or in part, the problems mentioned above.

For this purpose, the present disclosure relates to an implantation device, for implanting implants, for example semi-permanent type acupuncture needles, in the body of a living being, the implantation device comprising at least:

- a set of implants comprising at least two implants disposed successively along a line of implants, the implants being linked so that each implant can be separated from the set of implants,
- a guide member defining a passage which extends along the line of implants and up to an outlet port configured to be placed against the epidermis of the living being, the passage being configured to guide the set of implants in translation towards the outlet port and along the line of implants,
- a transmission member arranged to transmit a pushing force to the set of implants so as to move the set of implants in translation towards the outlet port and along the line of implants, the transmission member including a plurality of projections disposed successively along the line of implants,
- a pushing member configured to allow a practitioner to generate the pushing force, the pushing member being displaceable between a rest position and a pushing position, the pushing member including a bearing part configured to press successively against a plurality of projections during several successive displacements of the pushing member between the rest position and the pushing position, the bearing part being configured to present successively:
    - a bearing position, in which the bearing part presses against a respective projection during each displacement of the pushing member between the rest position and the pushing position, and
    - a crossing position, in which the bearing part is elastically deformed by the respective projection so that the bearing part can cross the projection when the pushing member undergoes a return force toward its rest position, the implantation device further comprising a one-way stop element which is linked to the guide member and configured to present successively:

- a crossing configuration, in which the one-way stop element is elastically deformed by one of the projections so that the projection can cross the one-way stop element, and
- a stop configuration, in which the one-way stop element abuts against one of the projections so as to immobilize the transmission member in the opposite direction to the translation towards the outlet port and along the line of implants.

Thus, such an implantation device allows the practitioner to implant several implants quickly and simply, because the implantation device can be easily manipulated. Therefore, such an implantation device decreases the duration of installation of the implants, which increases the comfort of the living being, for example of the patient.

In addition, such an implantation device reduces the implantation cost of several implants, since a single sterile implantation device allows implanting several implants, while a sterile implantation device of the prior art allowed to implant only one implant.

Furthermore, to install each implant of the set of implants, the practitioner exerts the same pushing force, which increases the accuracy of installation of the implants, because each single implantation device of the prior art requires a more or less specific pushing force, depending on the reproducibility in the manufacture of the single implantation devices. The practitioner can exert the pushing force by hand.

In the present application, the expression «in a reference direction» relates to a direction parallel or collinear with a reference direction. Similarly, the expression «along a reference line» relates to a line parallel or collinear with a reference line. For example, the expression «along the line of implants» relates to a curvilinear or rectilinear line parallel or collinear with the line of implants.

According to one variant, the line of implants is straight. In this variant, the translation of the set of implants is rectilinear. In this variant, the successive projections can be disposed parallel to the line of implants. In other words, the transmission member forms a kind of serrated rod, whose teeth are formed by the projections.

Alternately to this variant, the line of implants is curved with one or more curvature(s). In this variant, the translation of the set of implants is curvilinear. In this variant, dimensions and materials of the components of the implantation device are selected so that the set of implants can slide in the passage. The or each radius of curvature may for example be greater than 80 mm, to allow a translation of the set of implants with little friction against the passage.

In this variant, the pushing member is configured to be deformed during the curvilinear translation. In order to obtain this deformation of the pushing member, it is possible, for example, to form the pushing member by selecting a cross-section with a diameter of 1.3 mm, a length of 20 mm and a thermoplastic material such as Acrylonitrile Butadiene Styrene (ABS) or Polycarbonate (PC), which thus has an appropriate Young's modulus. In other words, the line of implants can be weakly bent. In this variant, the projections can be disposed on the curved line of implants.

According to one variant, the passage is in direct contact with the set of implants. In this variant, there is no intermediate component between the set of implants and the passage. Thus, the implantation device can be particularly compact according to directions perpendicular to the line of implants.

According to one variant, the pushing member comprises a gripping part configured to allow the practitioner to manipulate the implantation device.

According to one variant, the one-way stop element is secured to the guide member. For example, the one-way stop element and the guide member may be in one-piece. Alternately to this example, the one-way stop element and the guide member can be linked by elastic snap-fitting or by press-fitting.

According to one variant, the guide member is composed of a single part. Alternately to this embodiment, the guide member can be composed of at least two assembled parts.

According to one variant, the pushing member is composed of a single part. Alternately, to this embodiment, the pushing member can be composed of at least two assembled parts.

According to one embodiment, the implants are in contact two by two in the set of implants.

In other words, the implants are contiguous two by two in the set of implants. Thus, the set of implants is simple to assemble and particularly compact.

Alternately to this embodiment, the set of implants may comprise spacer elements disposed so that each spacer element links two implants together. In this variant, the implants are not in contact two by two, because each spacer element is interposed between two implants. The spacer elements may be for example caps each covering the needle of a respective implant. Thus, such spacer elements allow isolating and wrapping partially each implant in the set of implants.

According to one embodiment, each implant has a tip configured to penetrate the epidermis of the living being, and each implant has a housing which is located opposite the tip and configured to house at least partially the tip of the next implant.

Thus, in the set of implants, the implants are two by two linked together by a surface contact connection.

According to one variant, each implant has a cone, tetrahedron or pyramid-shaped tip. Alternately to this variant, each implant has a harpoon-shaped tip, that is to say with at least two hooks on either side of a central rod.

According to one variant, the set of implants and the passage are configured so that, before the first of the successive displacements, the distal implant is located entirely inside the passage. The distal implant designates the furthest implant from the transmission member, therefore the closest to the outlet port. Thus, the distal implant is not likely to reach an external object before being installed in the skin of the living being. The contamination of the distal implant before its implantation is thus avoided.

In the present application, the term «distal» designates an element which is relatively far from the pushing member, while the term «proximal» designates an element which is relatively close to the pushing member. For example, when the implantation device is in service, it is the distal implant that comes out first through the outlet port to penetrate the epidermis of the living being.

According to one embodiment, each housing is formed by a distal wall and a proximal opening, each tip and each housing being configured so that the solid angle defined by a respective tip is greater than a solid angle defined between the proximal opening and any point of the distal wall.

Thus, such solid angles prevent the end of each the tip from reaching the distal wall of the housing, which could blunt each tip housed in a respective housing.

In the variant where the translation of the set of implants is curvilinear, the difference between:
i) the solid angle defined by a respective tip
ii) the solid angle defined between the proximal opening and any point of the distal wall
is greater than or equal to 0.03 sr (steradians).

According to one variant, each implant is composed of a material selected from the group consisting of a medical grade stainless steel, a medical grade titanium alloy and a bioresorbable material. According to one variant, each implant has a length comprised between 1.5 mm and 5 mm, for example equal to 3 mm, and a dimension perpendicular to the length comprised between 0.5 mm and 3 mm, for example equal to 1.3 mm. Thus, such an implant can form an acupuncture needle suitable for auricular-therapy.

According to one variant, the set of implants comprises between two and ten implants, for example five implants. Thus, this number of implants forms a sufficient reserve for most of the procedures that a practitioner must perform, in particular in acupuncture.

According to one embodiment, the interval between distal ends of two successive implants being equal to the distance between distal ends of two successive projections.

In other words, this interval represents the step by which the set of implants advances with each displacement of the pushing member between the rest position and the pushing position.

Thus, such an interval makes it possible to store the implants in the implantation device in a relatively compact manner according to the line of implants.

According to one variant, the interval between distal ends of two successive implants being comprised between 1 mm and 4 mm, for example equal to 2.7 mm.

According to one variant, the passage has a proximal portion with substantially a constant size-section and a distal portion of a restricted section relative to the constant size-section. Thus, such a restricted section allows retaining the set of implants inside the passage in the absence of pushing force.

According to one variant, the restricted section is configured to be elastically deformed during successive crossings by the implants.

According to one embodiment, the implantation device comprises in addition a return member arranged to exert, on the pushing member, the return force towards the rest position.

Thus, such a return member simplifies the manipulation of the implantation device because the return member brings by itself the pushing member back to the rest position.

Alternately to the previous embodiment, the pushing member comprises a gripping portion configured to allow the practitioner to move the pushing member towards the rest position. In other words, the implantation device is devoid of a return member. Thus, the practitioner can bring the pushing member back to the rest position.

According to one variant, the return member is configured to work in compression against the pushing member and against the guide member.

According to one variant, the return member is elastically deformable.

Alternately to this variant, the return member can be configured to work in tension on the pushing member and on the guide member.

According to one variant, the return member comprises a helical spring. Thus, such a helical spring allows returning the pushing member to the rest position in a repeatable and durable way, because this helical spring has a constant stiffness over the service life.

In the variant where the helical spring is configured to work in tension, the helical spring can be sized so that the coils of the helical spring are joining when the helical spring is at rest. Coils joining in this way allow an easy assembly of the implantation device, in particular because these joining coils avoid the entanglement of several helical springs in the container of helical springs.

Alternately to this variant, the return member can be composed of a plastic, metallic or composite material. For example, the return member may be composed of an elastomer material or a thermoplastic elastomer material. In particular, the return member may comprise at least one material selected from the group consisting of a rubber, a latex, a silicone compound and an ethylene-propylene-diene monomer (EPDM).

According to one variant, the return member may be integral with a component of the implantation device, for example with the guide member or with the pushing member. This one-piece return member can be helical or not. Such a one-piece return member makes it possible to simplify the mounting of the implantation device, because it dispenses from positioning and assembling an independent return member, for example a helical spring made of a spring steel.

According to one embodiment, the guide member includes a guide surface, which is arranged to guide the pushing member in translation along the line of implants.

Thus, such a guide surface allows a translation of the pushing member, which allows it to exert the pushing force on the transmission member.

According to one variant, the guide surface is located on an outer portion of the guide member.

According to one variant, the guide surface has generally a prismatic or cylindrical shape whose axis is substantially parallel to the line of implants.

According to one variant, the guide surface has splines extending substantially parallel to the line of implants. Thus, such splines allow improving the sliding by allowing a dimensional tolerance.

According to one variant, the number of projections is greater than the number of implants, for example by one. Thus, such a number of projections guarantees that the practitioner can push all the implants contained in the implantation device.

According to one embodiment, the one-way stop element and the transmission member are configured to generate a characteristic noise, for example a clicking sound, when the one-way stop element switches from the crossing configuration to the stop configuration.

Thus, such a characteristic noise indicates to the practitioner that the one-way stop element has reached the stop configuration, so that the practitioner can stop exerting the pushing force on the pushing member.

According to one variant, the bearing part and the transmission member are configured to generate a characteristic noise, for example a clicking sound, when the one-way stop element switches from the crossing configuration to the stop configuration.

According to one embodiment, each projection has generally a frustoconical shape with a narrow part and a wide part, the narrow part being located closer to the outlet port than the wide part.

Thus, such a frustoconical shape facilitates the manufacture of the transmission member, the pushing member and the guide member, because they present symmetries of revolution. Moreover, this symmetry of revolution dispenses from orienting the transmission member during the assembly of the implantation device.

According to one variant, the transmission member has two opposite smooth faces, the projections being disposed at least on one face extending between the two opposite smooth faces, and each projection has generally a triangular prism shape with a narrow portion and a wide portion, the narrow portion being located closer to the outlet port than the wide portion.

In the present application, the term «smooth» designates an element, for example a face, which is devoid of projection. Nevertheless, a smooth face may be more or less rough. According to one variant, at least one of the two smooth faces is flat.

Thus, such a transmission member may have a particularly small bulk in a direction substantially perpendicular to the line of implants.

According to one variant, the triangular prism has, in cross-section, an angle comprised between 4 degrees and 30 degrees, for example equal to 8 degrees, the angle pointing towards the outlet port.

According to one variant, the projections are disposed on both faces extending between the two opposite smooth faces.

According to one embodiment, the pushing member comprises in addition a conduit configured to allow successive sliding movements of the projections in translation towards the outlet port and along the line of implants.

Thus, such a conduit makes it possible to support and guide the transmission member.

According to one embodiment, the guide member is translucent or transparent and in which the set of implants and/or the transmission member is/are totally or partially colored.

Thus, the practitioner can see through the guide member the number of implants still available. Advantageously, the transmission member and/or the set of implants is/are colored into at least one bright color.

According to one variant, the guide member, the transmission member and/or the pushing member are composed of medical grade plastic materials. Thus, the transmission member and/or the pushing member can be manufactured by injection molding with complex and economic shapes.

According to one embodiment of the preceding variant, the return member is integral with the pushing member or with the guide member, the return member being composed of a material having a Young's modulus less than 30 GPa, the return member having notches arranged substantially transversely to the line of implants so as to allow elastic deformation of the return member.

Thus, such a one-piece return member makes it possible to reduce the assembly costs of the implantation device, by eliminating the step of assembling an independent return member.

According to one variant, the transmission member has a smooth segment located on the proximal side of the most proximal projection.

Thus, such a smooth segment, therefore devoid of projection, prevents the pushing member to press against the transmission member when there are no more implants in the implantation device. Indeed, the most proximal projection is the projection that allows pushing the last implant out of the implantation device. Then, the bearing part of the pushing member slides on the smooth segment without pressing against the transmission member, because it can no longer press against a projection. The practitioner is thus informed that the implantation device no longer contains implants.

Alternately or complementarily to this variant, the transmission member has an abutment portion configured to abut against the bearing part. Thus, such an abutment portion cannot cross the bearing part, so that the return member cannot bring the pushing member back to the rest position.

Therefore, the practitioner understands that there are no more implants in the implantation device. The practitioner can then discard the used implantation device. In addition, the abutment portion may produce a characteristic noise by abutting against the bearing part, which points out to the practitioner that the implantation device is empty.

According to one variant, the abutment portion may have generally a cylindrical shape whose diameter is greater than the dimensions of the passage of the bearing part in the crossing position.

According to one variant, the transmission member is composed of a material selected from the group consisting of stainless steel, titanium alloy and thermoplastic of a density greater than 1000 kg/m$^3$ such as polyvinyl chloride (PVC), polycarbonate (PC) or acrylonitrile butadiene styrene (ABS).

According to one embodiment, the bearing part comprises at least two elastic portions separated by at least one slot.

Thus, such elastic portions allow the bearing part to present successively its bearing position, in which the elastic portions are at rest (not deformed), and its crossing position, in which the elastic portions are deformed by one of the projections, thereby allowing the bearing part to cross the projection when the pushing member returns to the rest position.

According to one embodiment, the one-way stop element comprises at least two elastic tabs separated by at least one notch.

Thus, such elastic tabs allow the one-way stop element to present successively i) its crossing configuration, in which the elastic tabs are deformed by one of the projections, and ii) its stop configuration, in which the elastic tabs are at rest (not deformed), thereby allowing the one-way stop element to abut against one of the projections and thus to immobilize the transmission member in the opposite direction to the translation towards the outlet port and along the line of implants.

According to one variant, the elastic tabs are configured to snap against a respective projection when the one-way stop element is in the stop configuration. Thus, the elastic tabs can snap against each projection, so as to generate the characteristic noise. In particular, the stiffness of the elastic tabs and the surface hardness of the transmission member are selected to obtain the characteristic noise.

According to one variant, the elastic portions are configured to snap against a respective projection when the one-way stop element is in the stop configuration. Thus, the elastic portions can snap against each projection, to generate the characteristic noise. In particular, the stiffness of the elastic portions and the surface hardness of the transmission member are selected to obtain the characteristic noise.

According to one variant, the implantation equipment also comprises at least one envelope composed of flexible plastic material surrounding the set of implants.

According to one variant, the implantation equipment also comprises an overpack, said envelope being disposed within the overpack.

The embodiments and variants mentioned above can be taken separately or in any technically possible combination.

BRIEF DESCRIPTION OF THE DRAWINGS

The present disclosure will be well understood and its advantages will also emerge in the light of the description that follows, given only by way of non-limiting example and with reference to the appended figures, in which identical reference signs correspond to structurally and/or functionally identical or similar elements.

In the figures.

DETAILED DESCRIPTION OF THE DRAWINGS

FIGS. 1 to 13 illustrate an implantation device 1 for implanting implants, in this case acupuncture needles, in the epidermis of a living being not represented.

The implantation device 1 comprises a set of implants 2. The set of implants 2 here comprises five implants 4 disposed successively along a line of implants X2. The line of implants X2 is straight.

The implants 4 are linked so that each implant 4 can be separated from the set of implants 2. The implants 4 are here in contact two by two, therefore contiguous, in the set of implants 2.

Figures 4, 5:
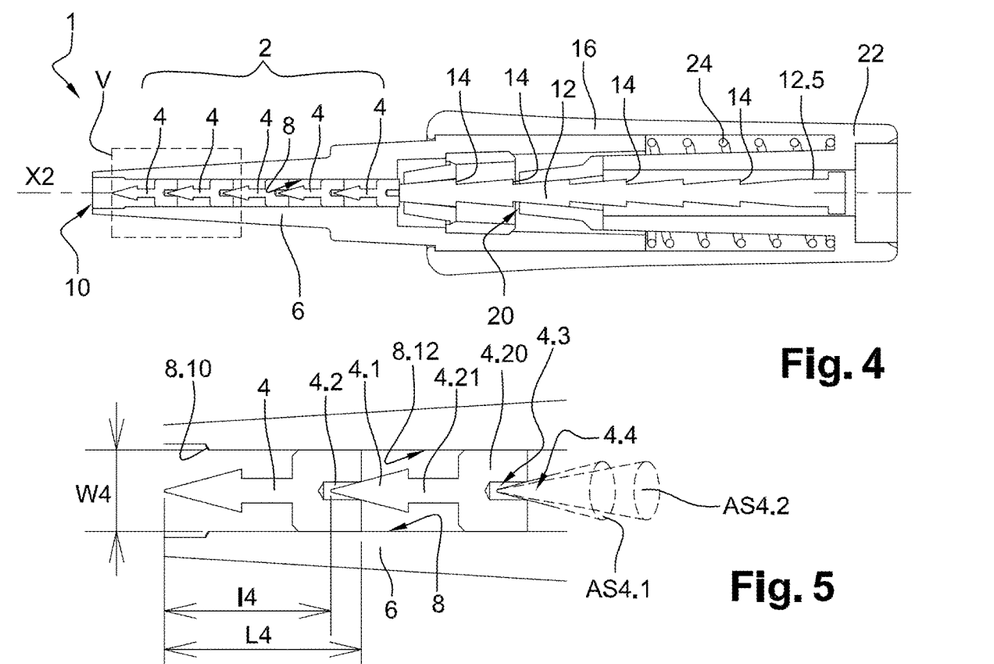
FIG. 4 is a schematic sectional view, along the plane IV in FIG. 1, of the implantation device of FIG. 1.
FIG. 5 is a view on a larger scale of the detail V in FIG. 4.

As shown in FIG. 5, each implant 4 has a length L4 approximately equal to 3 mm and a width W4, measured perpendicularly to the length L4 approximately equal to 1.3 mm. Each implant 4 is here composed of a medical grade stainless steel.

As shown in FIG. 5, each implant 4 has a tip 4.1 configured to penetrate into the epidermis of the living being. Each tip 4.1 is here in the form of a harpoon, which is to say with at least two hooks on either side of a central rod.

Each implant 4 has a housing 4.2, which is located opposite the tip 4.1 and configured to house at least partially the tip 4.1 of the next implant 4. Each housing 4.2 is arranged in a base 4.20 which is secured to the tip 4.1 by a rod 4.21 in the set of implants 2, the implants 4 are two by two linked together by a surface contact connection.

Each housing 4.2 is formed by a distal wall 4.3 and a proximal opening 4.4. Each tip 4.1 and each housing 4.2 are configured so that the solid angle AS4.1 defined by a respective tip is greater than a solid angle AS4.2 defined between the proximal opening 4.4 and any point on the distal wall 4.3.

For example, the solid angle AS4.1 may be approximately equal to 0.214 sr (namely a half-angle at the apex between the axis and the generatrix of the cone approximately equal to 15 degrees). For example, the solid angle AS4.2 can be at most equal to 0.185 sr. Thus, the difference between the solid angles AS4.1 and AS4.2 is greater than or equal to 0.03 sr (steradians).

In addition, the implantation device 1 comprises a guide member 6, which is here composed of a single part from the injection molding of a polyethylene (PE).

The guide member 6 defines a passage 8. The passage 8 extends along the line of implants X2 and up to an outlet port 10. The outlet port 10 is configured to be placed against the epidermis of the living being. The passage 8 is configured to guide the set of implants 2 in translation towards the outlet port and along the line of implants X2.

In the example of FIGS. 1 to 13, the passage 8 has generally a cylinder shape whose axis is collinear with the line of implants X2 and whose base has substantially the same transverse dimensions (width W4) as the implants 4. The passage 8 is here directly in contact with the set of implants 2.

The implantation device 1 further comprises a transmission member 12. The transmission member 12 is arranged to transmit a pushing force P2 (symbolized in FIG. 6) to the set of implants 2 in order to move the set of implants 2 in translation towards the outlet port 10 and along the line of implants X2. The transmission member 12 is here composed of a polyvinyl chloride (PVC).

Since the line of implants X2 is straight, the translation of the set of implants 2 is rectilinear. The transmission member 12 has here a distal pushing surface 13, which comes into contact with the proximal implant 4 in order to transmit the pushing force P2 to the set of implants 2.

In order to receive the pushing force P2, the transmission member 12 includes a plurality of projections 14. The projections 14 are disposed successively along the line of implants X2. In this case, the projections 14 are disposed parallel to the line of implants X2. In other words, the transmission member 12 forms a kind of serrated rod, whose teeth are formed by the projections 14.

The number of projections 14 is here greater by one than the number of implants 4. In the example of FIGS. 1 to 13, there are six projections 14 and five implants 4. Each projection 14 here has generally a frustoconical shape, with a narrow part and a wide part, the narrow part being located closer to the outlet port 10 than the wide part. In other words, the frustoconical surfaces of the projections 14 are oriented towards the outlet port 10.

In addition, the implantation device 1 comprises a pushing member 16, which is composed of a single part from the injection molding of a polyethylene (PE). The pushing member 16 is configured to allow a practitioner to generate the pushing force P2.

Figures 1, 2, 3:
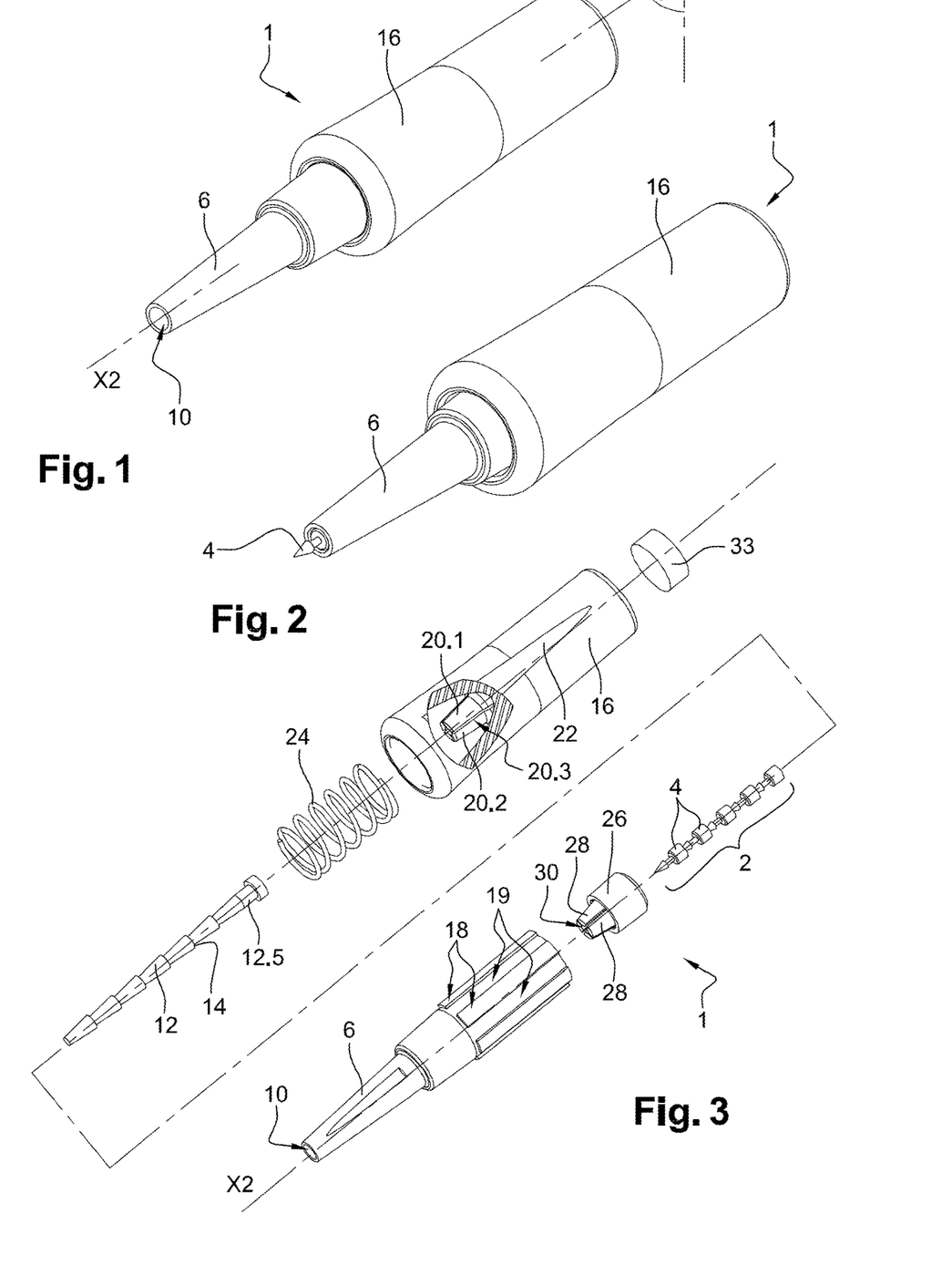
FIG. 1 is a schematic perspective view of an implantation device in accordance with a first embodiment of the disclosure, before the implantation of a first implant.
FIG. 2 is a schematic perspective view of the implantation device of FIG. 1, during the implantation of the first implant.
FIG. 3 is an exploded perspective view with a partial cutaway of the implantation device of FIGS. 1 and 2.

The pushing member 16 is displaceable between a rest position (FIGS. 1 and 7) and a pushing position (FIGS. 2 and 5). To this end, the guide member 6 includes a guide surface 18, which is arranged to guide the pushing member 12 in translation along the line of implants X2.

The guide surface 18 allows a translation of the pushing member 16. The guide surface 18 is here located on an outer portion of the guide member 6. The guide surface 18 here has generally a cylindrical shape whose axis is parallel to the line of implants X2.

Figures 13, 14:
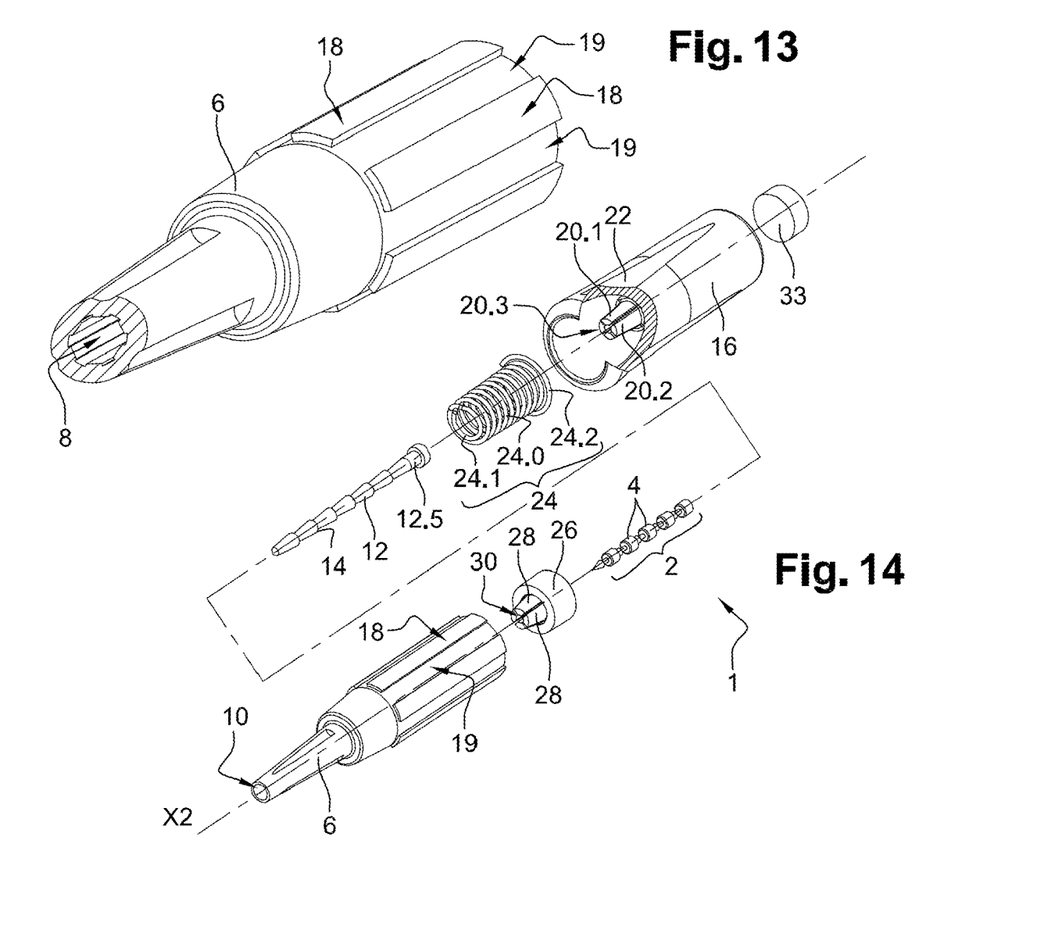
FIG. 13 is a detailed perspective view of the guide member belonging to the implantation device of FIG. 1.
FIG. 14 is a view similar to FIG. 3 of an implantation device in accordance with a second embodiment of the disclosure.
Figure 15:
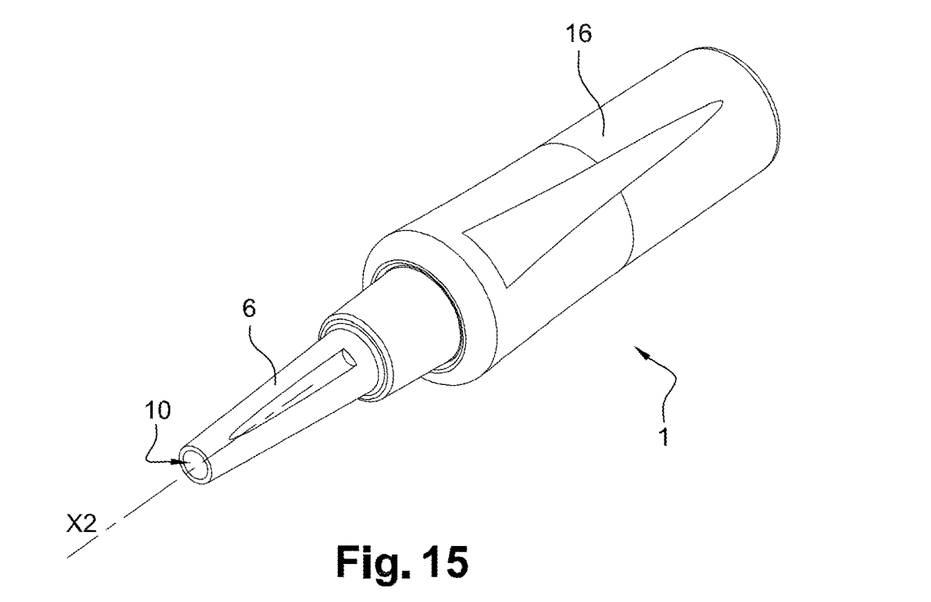
FIG. 15 is an assembled perspective view, similar to FIG. 1, of the implantation device of FIG. 14.
Figure 16:
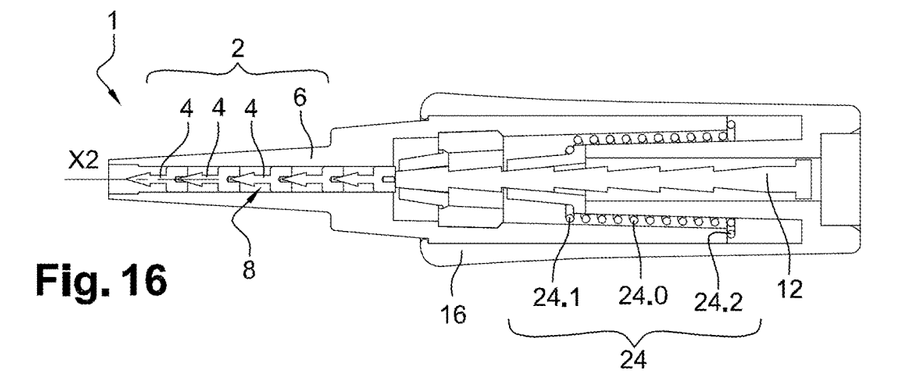
FIG. 16 is a median sectional view similar to FIG. 4 of the implantation device of FIG. 14, before the implantation of the first implant.
Figure 17:
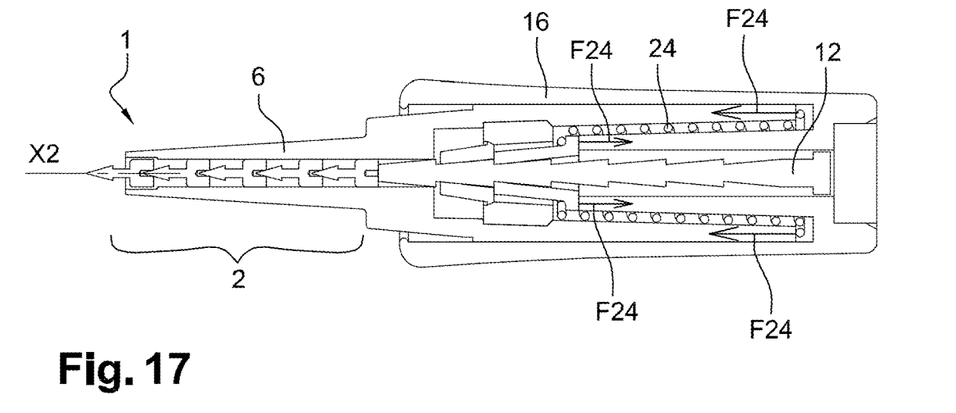
FIG. 17 is a view similar to FIG. 16 of the implantation device of FIG. 16, during the implantation of the first implant.

As shown in FIG. 13, the guide surface 18 presents splines 19 which extend substantially parallel to the line of implants X2. The splines 19 make it possible to improve the sliding by authorizing a dimensional tolerance.

The pushing member 16 includes a bearing part 20 which is configured to press successively against several projections 14 during several successive displacements of the pushing member 16 between the rest position (FIGS. 1 and 7) and the pushing position (FIGS. 2 and 5). The bearing part 20 here has an annular shape, because the pushing member 16 has a cylindrical distal portion with a circular base.

The set of implants 2 is configured so that, before the first of the successive displacements of the pushing member 16, the distal implant 4 is entirely located inside the passage 8. The distal implant 4 designates the implant 4 furthest from the transmission member 12, therefore the closest to the outlet port 10. Surrounded in this way, the distal implant 4 is not likely to reach an external object before being installed in the epidermis of the living being.

The interval 14 between distal ends of two successive implants 4 is here regular and approximately equal to 2.7 mm. This interval 14 between distal ends of two successive implants 4 is equal to the distance between distal ends of two successive projections 14. This interval represents the step by which the set of implants 4 advances with each displacement of the pushing member 16 between the rest position and the pushing position.

In addition, the pushing member 16 comprises a gripping part 22, which is configured to allow the practitioner to manipulate the implantation device 1. The pushing member 16 further comprises a conduit 17, which is configured to allow successive sliding movements of the projections 14 in translation towards the outlet port 10 and along the line of implants X2. In service, the conduit 17 supports and guides the transmission member 12.

Figure 7:
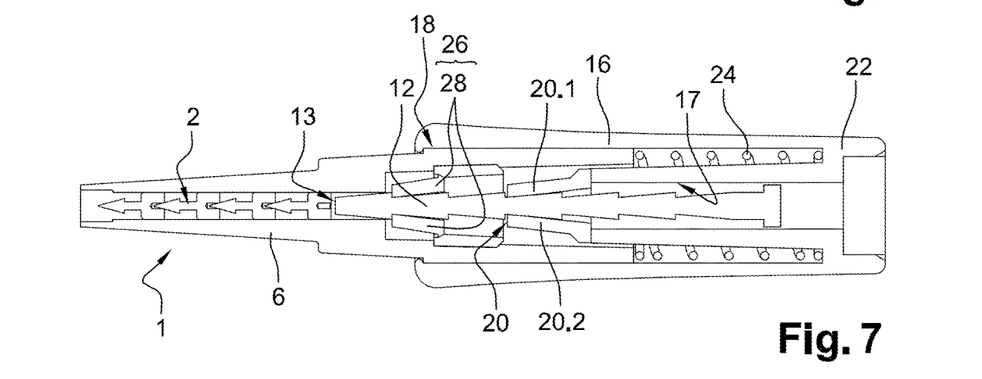
FIG. 7 is a view similar to FIG. 6 of the implantation device of FIG. 2, after the implantation of the first implant.

The implantation device 1 furthermore comprises a return member 24, which is here elastically deformable. The return member 24 is arranged to exert, on the pushing member 16, a return force F24 towards the rest position (FIGS. 1 and 7).

In the example of FIGS. 1 to 13, the return member 24 comprises a helical spring which is configured to work in compression against the pushing member 16 and against the guide member 6. In service, this helical spring allows returning the pushing member 16 to the rest position.

The bearing part 20 here comprises two elastic portions 20.1 and 20.2, which are separated by a slot 20.3. The bearing part 20 is configured to present successively:
  a bearing position (FIGS. 4, 6 and 7), in which the bearing part 20 bears against a respective projection 14 during each displacement of the pushing member 16 between the rest position and the pushing position (FIG. 6), and
  a crossing position similar to the position shown in FIG. 12, in which the bearing part 20 is elastically deformed by the respective projection 14 so that the bearing part 20 can cross the projection 14 when the return member 24 exerts on the pushing member 16 the return force F24 towards the rest position.

The elastic portions 20.1 and 20.2 allow the bearing part 20 to present successively:
  i) its bearing position, in which the elastic portions 20.1 and 20.2 are at rest, therefore not deformed, and
  (ii) its crossing position, in which the elastic portions 20.1 and 20.2 are deformed by one of the projections 14, which allows the bearing part 20 to cross the projection 14 when the pushing member 16 returns to the rest position.

Figure 6:
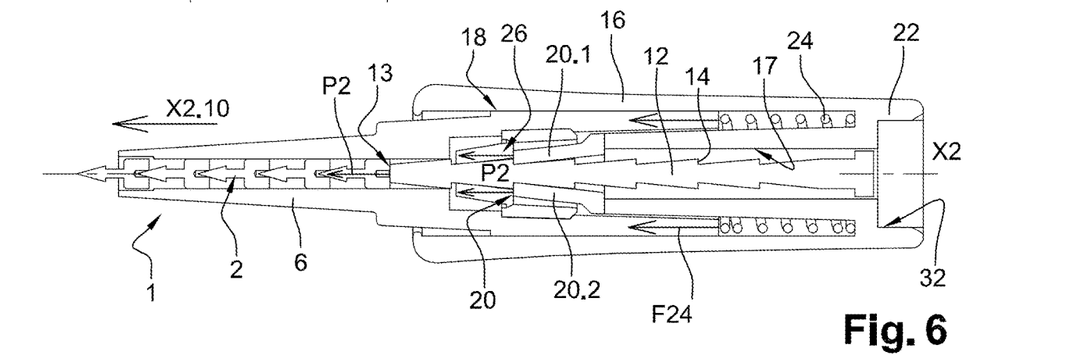
FIG. 6 is a view similar to FIG. 4 of the implantation device of FIG. 2 during the implantation of the first implant.

The bearing part 20 makes it possible, by its bearing against a projection 14, to transmit the pushing force P2 of the pushing member 16 to the transmission member 12, then, by its elastic deformation, to let the pushing member 16 return to its rest position (FIG. 7), before performing a new displacement towards the pushing position (FIG. 6).

In addition, the implantation device 1 comprises a one-way stop element 26 which is linked to the guide member 6 and configured to present successively:
  a crossing configuration, in which the one-way stop element 26 is elastically deformed by one of the projections 14 so that the projection 14 can cross the one-way stop element 26, and
  a stop configuration (FIGS. 4, 6 and 7), in which the one-way stop element 26 abuts against one of the projections 14 so as to immobilize the transmission member 12 in the opposite direction to the translation towards the outlet port 10 and along the line of implants X2, that is to say in the direction of the arrow X2.10 in FIG. 6.

In the example of FIGS. 1 to 13, the one-way stop element 26 is secured to the guide member 6. In this case, the one-way stop element 26 and the guide member 6 are in one-piece.

Figures 11, 12:
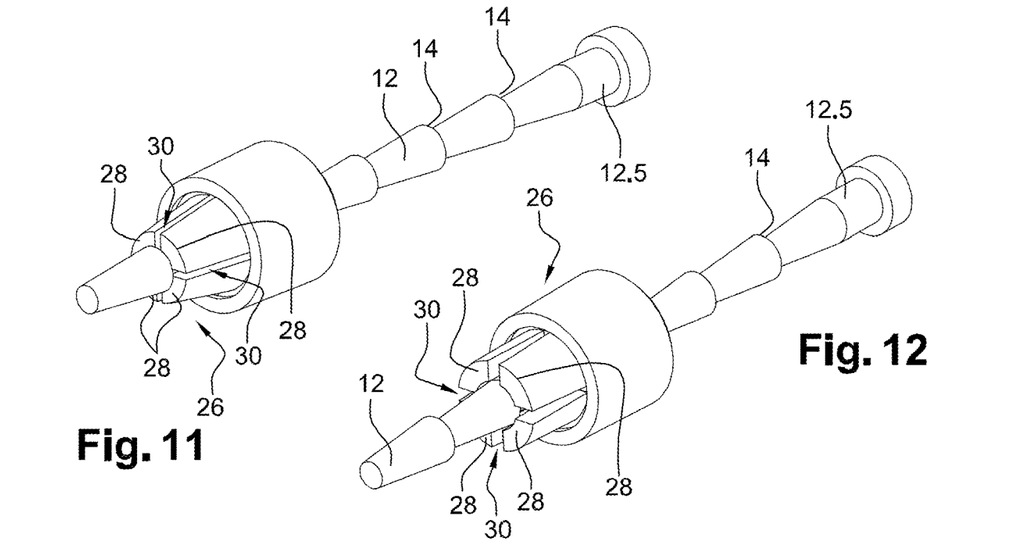
FIG. 11 is a schematic perspective view of a part of the implantation device of FIG. 1, before the transmission of a pushing force.
FIG. 12 is a view similar to FIG. 11, during the transmission of a pushing force.

As shown in FIGS. 11 and 12, the one-way stop element 26 comprises four elastic tabs 28, which are separated by two notches 30. These elastic tabs 28 allow the one-way stop element 26 to present successively:
  i) its crossing configuration, in which the elastic tabs 28 are deformed by one of the projections 14, and
  ii) its stop configuration (FIGS. 4, 6 and 7), in which the elastic tabs 28 are at rest (not deformed), which allows the one-way stop element 26 to abut against one of the projections 14 and thus to immobilize the transmission member 12 in the opposite direction to the translation towards the outlet port 10 and along the line of implants X2.

The passage 8 has a proximal portion 8.12 with substantially a constant size-section and a distal portion 8.10 of a restricted section relative to the constant size-section. In service, the restricted section allows retaining the set of implants 2 inside the passage 8 in the absence of pushing force P2. The restricted section is here configured to be elastically deformed during successive crossings by the implants 4.

Moreover, the one-way stop element 26 and the transmission member 12 are configured to generate a characteristic noise, here a clicking sound, when the one-way stop element 26 switches from the crossing configuration to the stop configuration (FIGS. 4, 6 and 7). In particular, the elastic tabs 28 are configured to snap against a respective projection 14 when the one-way stop element 26 is in the stop configuration.

To this end, the stiffness of the elastic tabs 28 and the surface hardness of the transmission member 12 are selected to obtain the clicking sound. In service, the elastic tabs 28 snap against each projection 14, which generates the clicking sound.

Figure 8:
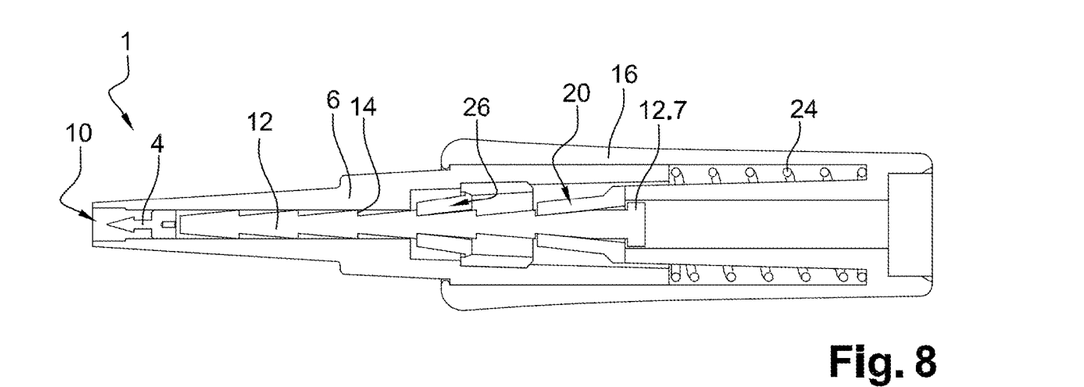
FIG. 8 is a view similar to FIG. 4 of the implantation device of FIG. 2, before the implantation of the last implant.
Figure 9:
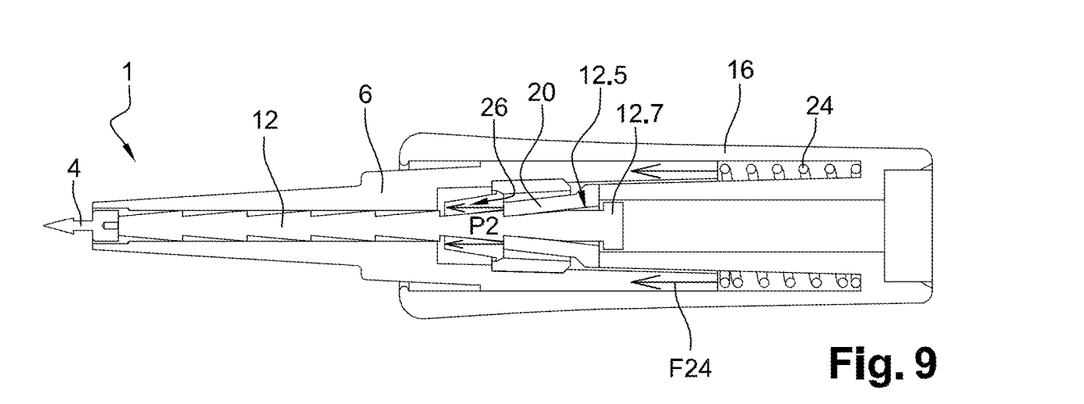
FIG. 9 is a view similar to FIG. 4 of the implantation device of FIG. 2, during the implantation of the last implant.
Figure 10:
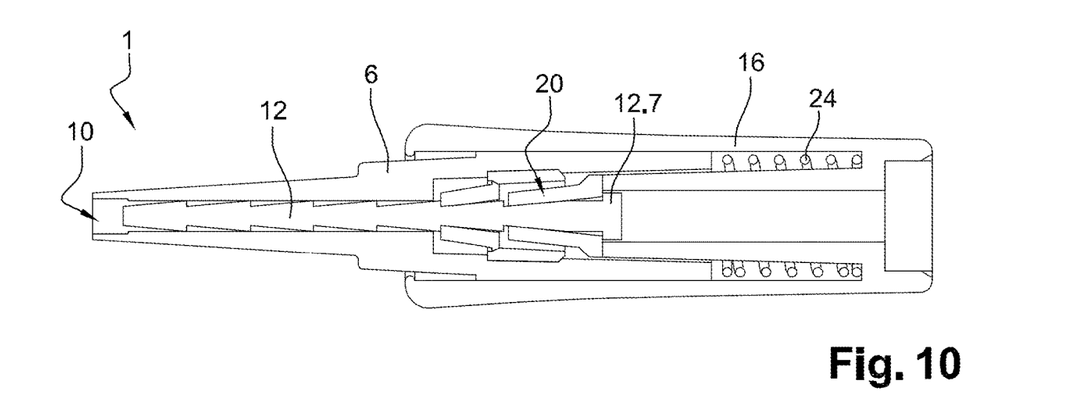
FIG. 10 is a view similar to FIG. 6 of the implantation device of FIG. 2, after the implantation of the last implant.

FIGS. 8 to 10 illustrate the implantation device 1 during the implantation of the last implant 4 or proximal implant. In this state, the set of implants 2 no longer comprises an implant 4.

The transmission member 12 here has a smooth segment 12.5, which is located on the proximal side of the most proximal projection 14. The smooth segment 12.5, devoid of projection 14, prevents the pushing member 16 from pressing against the transmission member 12 when there are no more implants 4 in the implantation device 1.

Indeed, the most proximal projection 14 is the projection, which allows pushing the last implant 4 out of the implantation device 1. Then, the bearing part 20 slides on the smooth segment 12.5 without pressing against the transmission member 12, because the bearing part 20 can no longer press against a projection 14.

In addition, the transmission member 12 has an abutment portion 12.7, which is configured to abut against the bearing part 20. The abutment portion 12.7 cannot cross the bearing part 20, so that the return member 24 cannot bring the pushing member back to the rest position.

The practitioner understands that there are no more implants in the implantation device 1 and then can discard the used implantation device. In the example of FIGS. 8, 9 and 10, the abutment portion 12.7 has generally a cylindrical shape whose diameter is greater than the dimensions of the passage of the bearing part 20 in the crossing position.

The guide member 6 may be translucent and the set of implants 2 and/or the transmission member 12 may be colored. Thus, the practitioner can see through the guide member 6 the number of implants 4 still available.

Furthermore, the pushing member 16 comprises a housing 32, which can be used to house a magnet 33 shown in FIG. 3. The housing 32 is here arranged on an end portion of the pushing member opposite to the set of implants 2.

FIGS. 14 to 17 illustrate an implantation device 1 in accordance with a second embodiment. To the extent that the implantation device 1 of FIGS. 14 to 17 is similar to the implantation device 1 of FIGS. 1 to 13, the description of the implantation device 1 given above in relation to FIGS. 1 to 13 may be transposed to the implantation device 1 of FIGS. 14 to 17, except for the notable differences set out below.

The implantation device 1 of FIGS. 14 to 17 differs from the implantation device 1 of FIGS. 1 to 13, because the return member 24 comprises a helical spring which is configured to work in tension on the pushing member 16 and on the guide member 6.

The return member 24 here has i) end portions 24.1 and 24.2, which are located respectively at both ends of the return member, and ii) an intermediate portion 24.0 which extends between the end portions 24.1 and 24.2. Each end portion 24.1 or 24.2 is formed by an end coil. The intermediate portion 24.0 comprises several coils.

The end portion 24.1 is arranged to bear against a complementary surface secured to the guiding member 6. Similarly, the end portion 24.2 is arranged to bear against a complementary surface secured to the pushing member 16 and here belonging to the bearing part 20. Thus, the return member 24 is arranged to work in tension.

In service, this helical spring makes it possible to recall the pushing member 16 to the rest position. This helical spring exerts a return force F24 on the pushing member 16 and on the guide member 6.

Figure 18:
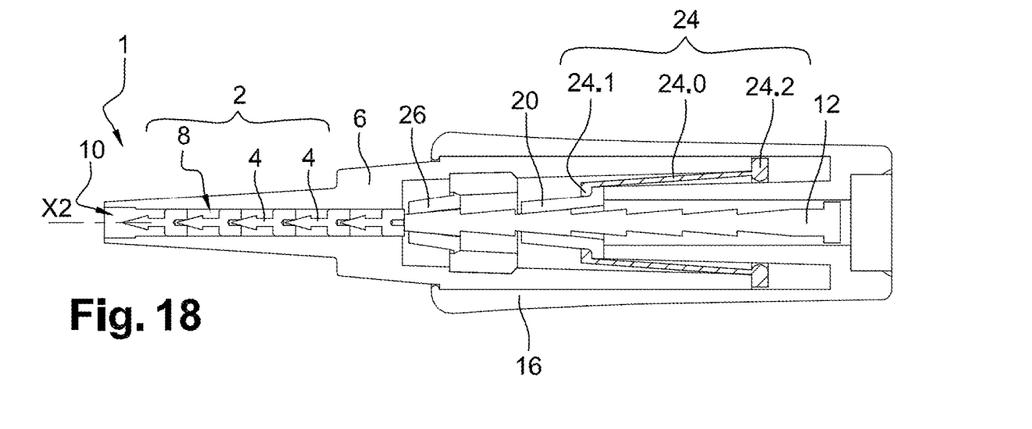
FIG. 18 is a median sectional view similar to FIG. 4 of an implantation device in accordance with a third embodiment of the disclosure, before the implantation of the first implant.
Figure 19:
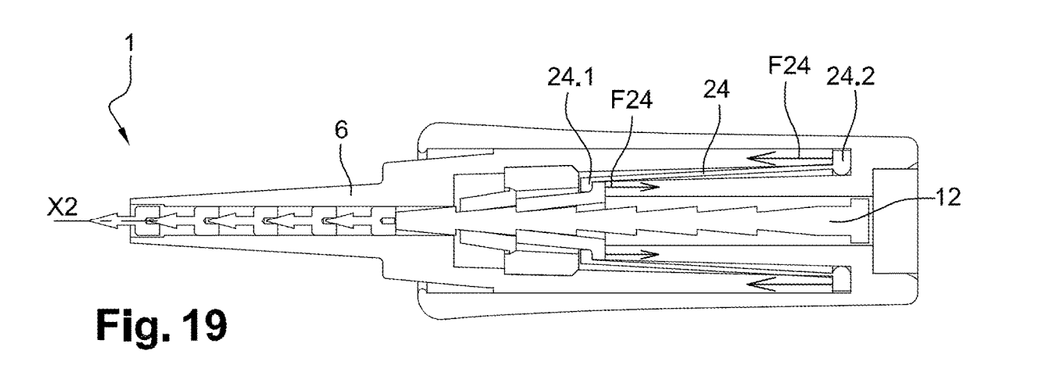
FIG. 19 is a view similar to FIG. 18 of the implantation device of FIG. 18, during the implantation of the first implant.

FIGS. 18 and 19 illustrate an implantation device 1 according to a third embodiment. To the extent that the implantation device 1 of FIGS. 18 and 19 is similar to the implantation device 1 of FIGS. 14 to 17, the description of the implantation device 1 given above in relation to FIGS. 14 to 17 may be transposed to the implantation device 1 of FIGS. 18 and 19, except for the notable differences set out below.

The implantation device 1 of FIGS. 18 and 19 differs from the implantation device 1 of FIGS. 14 to 17, because the return member 24 of FIGS. 18 and 19 is composed of an elastomer material, in this case a rubber. In service, the return member 24 makes it possible to recall the pushing member 16 towards the rest position.

The return member 24 here has i) end portions 24.1 and 24.2, which are located respectively at both ends of the return member, and ii) an intermediate portion 24.0 which extends between the end portions 24.1 and 24.2. Each end portion 24.1 or 24.2 has generally an annular shape. The intermediate portion 24.0 has generally a tubular shape.

The end portion 24.1 is arranged to bear against a complementary surface secured to the guide member 6. Similarly, the end portion 24.2 is arranged to bear against a complementary surface secured to the pushing member 16 and here belonging to the bearing part 20. Thus, the return member 24 is arranged to work in tension, just like the return member 24 of the implantation device 1 of FIGS. 14 to 17.

As shown in the comparison of FIGS. 18 and 19, the return member 24 stretches when the pushing member is moved so as to push an implant 4 out of the passage 8. This elastic deformation generates a return force F24 which is exerted by the annular portion 24.1 on the guide member 6 and by the annular portion 24.2 on the pushing member 16.

Figure 20:
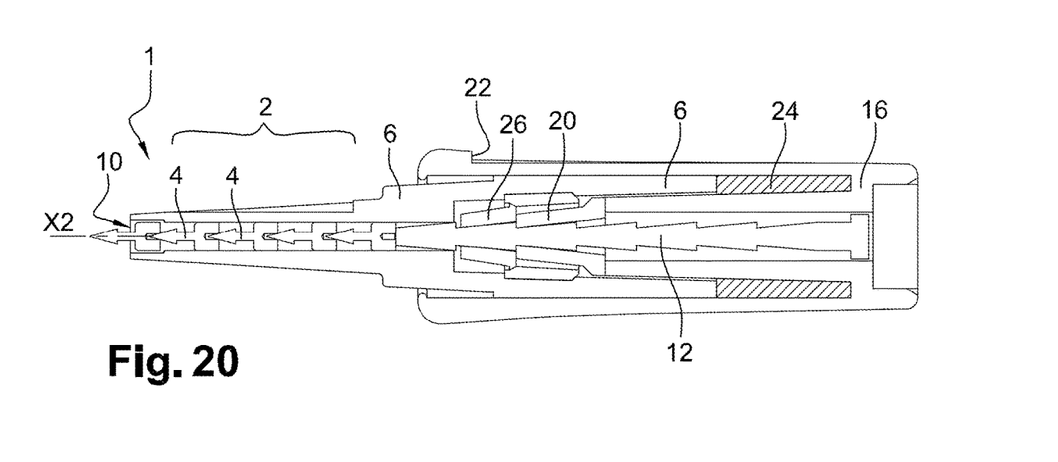
FIG. 20 is a sectional view similar to FIG. 4 of an implantation device in accordance with a fourth embodiment of the disclosure, during the implantation of the first implant.

FIG. 20 illustrates an implantation device 1 in accordance with a third embodiment. To the extent that the implantation device 1 of FIG. 20 is similar to the implantation device 1 of FIGS. 18 and 19, the description of the implantation device 1 given above in relation to FIGS. 18 and 19 may be transposed to the implantation device 1 of FIG. 20, except for the notable differences set out below.

The implantation device 1 of FIG. 20 differs from the implantation device 1 of FIGS. 18 and 19, because the return member 24 of FIG. 20 is arranged to work in compression, just like the return member 24 of the implantation device 1 of FIGS. 1 to 13. The return member 24 of FIG. 20 is here formed only of a tube segment.

Figures 21, 22, 23:
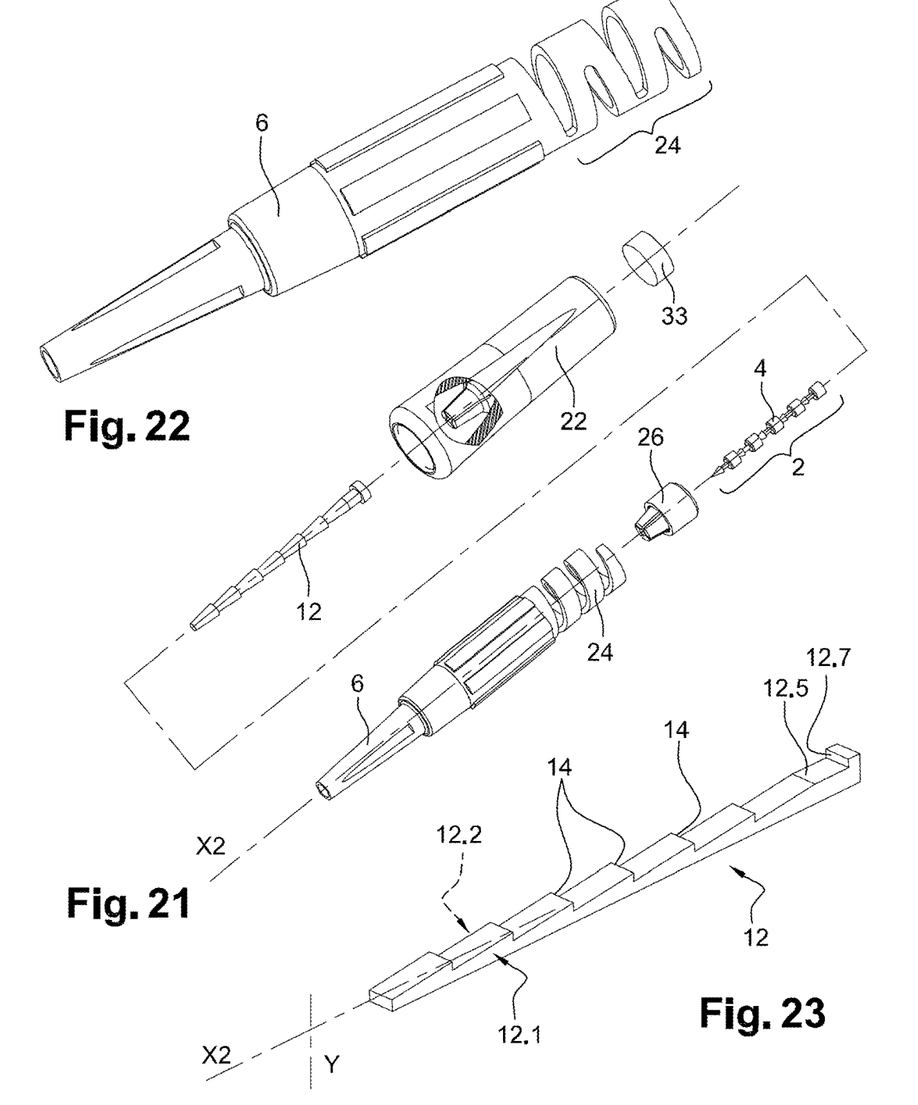
FIG. 21 is an exploded perspective view, similar to FIG. 3, of an implantation device in accordance with a fifth embodiment of the disclosure.
FIG. 22 is a perspective view of the guide member belonging to an implantation device in accordance with a sixth embodiment of the disclosure.
FIG. 23 is a perspective view of the transmission member belonging to an implantation device according to a seventh embodiment of the disclosure.

FIG. 21 illustrates an implantation device 1 in accordance with a third embodiment. To the extent that the implantation device 1 of FIG. 21 is similar to the implantation device 1 of FIGS. 1 to 13, the description of the implantation device 1 given above in relation to FIGS. 1 to 13 may be transposed to the implantation device 1 of FIG. 21, except for the notable differences set out below.

The implantation device 1 of FIG. 21 differs from the implantation device 1 of FIGS. 1 to 13, because the return member 24 of FIG. 21 is here integral (therefore in one-piece) with the guide member 6, which simplifies the mounting of the implantation device 1 of FIG. 21.

Just like the return member 24 of FIGS. 1 to 13, the one-piece return member 24 has a helical shape and is configured to work in compression between the guide member 6 and the pushing member 16. In the example of FIG. 21, the return member 24 and the guide member 6 are composed of injectable plastic material having a sufficient Young's modulus to create the return force, typically more than 10 MPa.

FIG. 22 illustrates part of an implantation device in accordance with a third embodiment. To the extent that the implantation device of FIG. 22 is similar to the implantation device 1 of FIG. 21, the description of the implantation device 1 given above in relation to FIG. 21 may be transposed to the implantation device of FIG. 22, except for the notable differences noted below.

The implantation device of FIG. 22 differs from the implantation device 1 of FIG. 21, because the return member 24 of FIG. 22 is formed by joining coils two by two, while the one-piece return member 24 of FIG. 21 has a regular helical shape. The particular shape of the return member 24 of FIG. 22 allows the molding in a mold having a parting joint parallel to the line of implants X2. In addition, the particular shape of the return member 24 of FIG. 22 can accommodate quite low Young's moduli (<10 MPa).

Moreover, the return member 24 of FIG. 22 is integral with the guide member 6, as the return member 24 of FIG. 21.

FIG. 23 illustrates part of an implantation device in accordance with a third embodiment. To the extent that the implantation device of FIG. 23 is similar to the implantation device 1 of FIGS. 1 to 13, the description of the implantation device 1 given above in relation to FIGS. 1 to 13 may be transposed to the implantation device of FIG. 23, except for the notable differences set out below.

The implantation device of FIG. 23 differs from the implantation device 1 of FIGS. 1 to 13, because the transmission member 12 presents two opposite smooth faces 12.1 and 12.2, and because each projection 14 has generally a triangular prism shape, while the transmission member 12 is formed by projections 14 of frustoconical shapes.

On the transmission member of FIG. 23, the projections 14 are disposed on a face extending between the two opposite smooth faces 12.1 and 12.2. Each projection 14 has generally a triangular prism shape with a narrow portion and a wide portion, the narrow portion being located closer of the outlet port 10 than the wide portion. Each triangular prism has, in cross-section, an angle which is approximately equal to 8 degrees and which points towards the outlet port 10.

Thus, this transmission member 12 has a particularly weak bulk in a direction Y substantially perpendicular to the line of implants X2.

Figure 24:
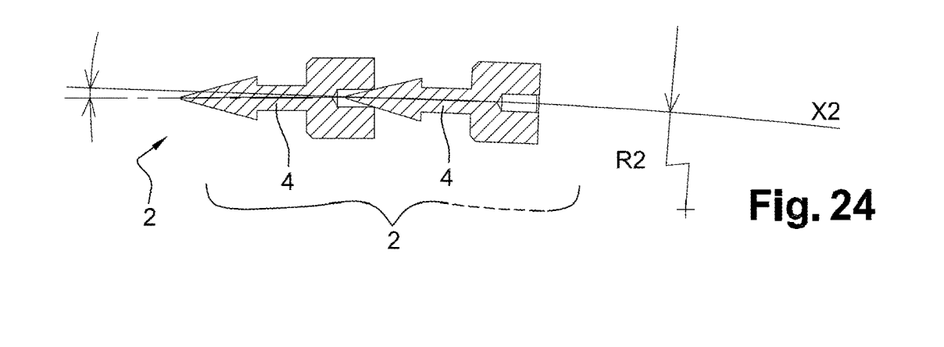
FIG. 24 is a sectional view of a part of a series of implants belonging to an implantation device in accordance with an eighth embodiment of the disclosure.

FIG. 24 illustrates part of an implantation device in accordance with a third embodiment. To the extent that the implantation device of FIG. 24 is similar to the implantation device 1 of FIGS. 1 to 13, the description of the implantation device 1 given above in relation to FIGS. 1 to 13 may be transposed to the implantation device of FIG. 24, except for the notable differences set out below.

The implantation device of FIG. 24 differs from the implantation device 1 of FIGS. 1 to 13, because the line of implants X2 is curved with a curvature. When the implantation device of FIG. 24 is in service, the translation of the set of implants 2 is here curvilinear.

The dimensions and materials of the components of the implantation device of FIG. 24 are selected so that the set of implants 2 can slide in the passage 8. The radius of curvature is here approximately equal to 80 mm. The pushing member not shown is configured to be deformed during the curvilinear translation of the set of implants 2.

Of course, the present disclosure is not limited to the particular embodiments described in the present patent application, or to embodiments within the reach of those skilled in the art. Other embodiments can be envisaged without departing from the scope of the disclosure, from any element equivalent to an element indicated in the present patent application.

The invention claimed is:

1. An implantation device, for implanting implants, in the body of a living being, the implantation device comprising at least:
    an implant set comprising at least two implants disposed successively along a line of implants, the implants being linked so that each implant is configured to separate from the implant set,
    a guide member defining a passage which extends along the line of implants and up to an outlet port configured to be placed against the epidermis of the living being, the passage being configured to guide the implant set in translation towards the outlet port and along the line of implants,
    a transmission member arranged to transmit a pushing force to the set of implants so as to move the implant set in translation towards the outlet port and along the line of implants, the transmission member including a plurality of projections disposed successively along the line of implants,
    a pushing member configured to allow a practitioner to generate the pushing force, the pushing member being displaceable between a rest position and a pushing position, the pushing member including a bearing part configured to press successively against several of the projections during several successive displacements of the pushing member between the rest position and the pushing position, the bearing part being configured to present successively:
    a bearing position, in which the bearing part presses against a respective projection during each displacement of the pushing member between the rest position and the pushing position, and
    a crossing position, in which the bearing part is elastically deformed by the respective projection so that the bearing part can cross the projection when the pushing member undergoes a return force towards its rest position,
    the implantation device further comprising a one-way stop element which is linked to the guide member and which is configured to present successively:
    a crossing configuration, in which the one-way stop element is elastically deformed by one of the projections so that the projection can cross the one-way stop element, and
    a stop configuration, in which the one-way stop element abuts against one of the projections so as to immobilize the transmission member in the opposite direction to the translation towards the outlet port and along the line of implants; and
    wherein the guide member is translucent or transparent and in which the implant set and/or the transmission member is/are totally or partially colored.

2. The implantation device according to claim 1, wherein the implants are in contact two by two in the implant set.

3. The implantation device according to claim 2, wherein each implant has a tip configured to penetrate in the epidermis of the living being, and wherein each implant has a housing which is located opposite the tip and which is configured to house at least partially the tip of the next implant.

4. The implantation device according to claim 3, wherein each housing is formed by a distal wall and a proximal opening, each tip and each housing being configured so that the solid angle defined by a respective tip is greater than a solid angle defined between the proximal opening and any point of the distal wall.

5. The implantation device according to claim 1, wherein the interval between distal ends of two successive implants is equal to the distance between distal ends of two successive projections.

6. The implantation device according to claim 1, further comprising a return member arranged to exert, on the pushing member, the return force towards the rest position.

7. The implantation device according to claim 1, wherein the guide member includes a guide surface which is arranged to guide the pushing member in translation along the line of implants.

8. The implantation device according to claim 1, wherein the one-way stop element and the transmission member are configured to generate a characteristic noise, for example a clicking sound, when the one-way stop element switches from the crossing configuration to the stop configuration.

9. The implantation device according to claim 1, wherein each projection has generally a frustoconical shape having a narrow part and a wide part, the narrow part being located closer to the outlet port than the wide part.

10. The implantation device according to claim 1, wherein the pushing member further comprises a conduit configured to allow successive sliding movements of the projections in translation towards the outlet port and along the line of implants.

11. The implantation device according to claim 1, wherein the return member is integral with the pushing member or with the guide member, the return member being composed of a material having a Young's modulus less than 30 GPa, the return member having notches arranged substantially transversely to the line of implants so as to allow an elastic deformation of the return member.

12. An implantation device, for implanting implants, for example semi-permanent type acupuncture needles, in the body of a living being, the implantation device comprising at least:
    an implant set comprising at least two implants disposed successively along a line of implants, the implants being linked so that each implant is configured to separate from the implant set,
    a guide member defining a passage which extends along the line of implants and up to an outlet port configured to be placed against the epidermis of the living being, the passage being configured to guide the implant set in translation towards the outlet port and along the line of implants,
    a transmission member arranged to transmit a pushing force to the implant set so as to move the implant set in translation towards the outlet port and along the line of implants, the transmission member including a plurality of projections disposed successively along the line of implants,
    a pushing member configured to allow a practitioner to generate the pushing force, the pushing member being displaceable between a rest position and a pushing position, the pushing member including a bearing part configured to press successively against several of the projections during several successive displacements of the pushing member between the rest position and the pushing position, the bearing part being configured to present successively:
    a bearing position, in which the bearing part presses against a respective projection during each displacement of the pushing member between the rest position and the pushing position, and
    a crossing position, in which the bearing part is elastically deformed by the respective projection so that the bearing part can cross the projection when the pushing member undergoes a return force towards its rest position,
    the implantation device further comprising a one-way stop element which is linked to the guide member and which is configured to present successively:
    a crossing configuration, in which the one-way stop element is elastically deformed by one of the projections so that the projection can cross the one-way stop element, and
    a stop configuration, in which the one-way stop element abuts against one of the projections so as to immobilize the transmission member in the opposite direction to the translation towards the outlet port and along the line of implants; and
    wherein the bearing part comprises at least two elastic portions separated by at least one slot.

13. The implantation device according to claim 12, wherein the implants are in contact two by two in the implant set.

14. The implantation device according to claim 13, wherein each implant has a tip configured to penetrate in the epidermis of the living being, and wherein each implant has a housing which is located opposite the tip and which is configured to house at least partially the tip of the next implant.

15. The implantation device according to claim 14, wherein each housing is formed by a distal wall and a proximal opening, each tip and each housing being configured so that the solid angle defined by a respective tip is greater than a solid angle defined between the proximal opening and any point of the distal wall.

16. The implantation device according to claim 12, wherein the interval between distal ends of two successive implants is equal to the distance between distal ends of two successive projections.

17. The implantation device according to claim 12, further comprising a return member arranged to exert, on the pushing member, the return force towards the rest position.

18. The implantation device according to claim 12, wherein the guide member includes a guide surface which is arranged to guide the pushing member in translation along the line of implants.

19. The implantation device according to claim 12, wherein the one-way stop element and the transmission member are configured to generate a characteristic noise, for example a clicking sound, when the one-way stop element switches from the crossing configuration to the stop configuration.

20. The implantation device according to claim 12, wherein each projection has generally a frustoconical shape having a narrow part and a wide part, the narrow part being located closer to the outlet port than the wide part.

21. The implantation device according to claim 12, wherein the pushing member further comprises a conduit configured to allow successive sliding movements of the projections in translation towards the outlet port and along the line of implants.

22. An implantation device, for implanting implants, for example semi-permanent type acupuncture needles, in the body of a living being, the implantation device comprising at least:
    an implant set comprising at least two implants disposed successively along a line of implants, the implants being linked so that each implant is configured to separate from the implant set,
    a guide member defining a passage which extends along the line of implants and up to an outlet port configured to be placed against the epidermis of the living being, the passage being configured to guide the implant set in translation towards the outlet port and along the line of implants,
    a transmission member arranged to transmit a pushing force to the implant set so as to move the implant set in translation towards the outlet port and along the line of implants, the transmission member including a plurality of projections disposed successively along the line of implants,
    a pushing member configured to allow a practitioner to generate the pushing force, the pushing member being displaceable between a rest position and a pushing position, the pushing member including a bearing part configured to press successively against several of the projections during several successive displacements of the pushing member between the rest position and the pushing position, the bearing part being configured to present successively:

a bearing position, in which the bearing part presses against a respective projection during each displacement of the pushing member between the rest position and the pushing position, and a crossing position, in which the bearing part is elastically deformed by the respective projection so that the bearing part can cross the projection when the pushing member undergoes a return force towards its rest position, the implantation device further comprising a one-way stop element which is linked to the guide member and which is configured to present successively:

a crossing configuration, in which the one-way stop element is elastically deformed by one of the projections so that the projection can cross the one-way stop element, and a stop configuration, in which the one-way stop element abuts against one of the projections so as to immobilize the transmission member in the opposite direction to the translation towards the outlet port and along the line of implants; and wherein the one-way stop member comprises at least two elastic tabs separated by at least one notch.

23. The implantation device according to claim 22, wherein the implants are in contact two by two in the implant set.

24. The implantation device according to claim 23, wherein each implant has a tip configured to penetrate in the epidermis of the living being, and wherein each implant has a housing which is located opposite the tip and which is configured to house at least partially the tip of the next implant.

25. The implantation device according to claim 24, wherein each housing is formed by a distal wall and a proximal opening, each tip and each housing being configured so that the solid angle defined by a respective tip is greater than a solid angle defined between the proximal opening and any point of the distal wall.

26. The implantation device according to claim 22, wherein the interval between distal ends of two successive implants is equal to the distance between distal ends of two successive projections.

27. The implantation device according to claim 22, further comprising a return member arranged to exert, on the pushing member, the return force towards the rest position.

28. The implantation device according to claim 22, wherein the guide member includes a guide surface which is arranged to guide the pushing member in translation along the line of implants.

29. The implantation device according to claim 22, wherein the one-way stop element and the transmission member are configured to generate a characteristic noise, for example a clicking sound, when the one-way stop element switches from the crossing configuration to the stop configuration.

30. The implantation device according to claim 22, wherein each projection has generally a frustoconical shape having a narrow part and a wide part, the narrow part being located closer to the outlet port than the wide part.

31. The implantation device according to claim 22, wherein the pushing member further comprises a conduit configured to allow successive sliding movements of the projections in translation towards the outlet port and along the line of implants.

* * * * *